United States Patent [19]

Wilhelm et al.

[11] Patent Number: 4,740,763
[45] Date of Patent: Apr. 26, 1988

[54] MICROWAVE CALORIMETER

[75] Inventors: Rolf Wilhelm, Calw-Stammheim; Paul G. Schüller, Stuttgart, both of Fed. Rep. of Germany

[73] Assignee: Max-Planck-Gesellschaft zur Foerderung der Wissenschaften e.V., Goettingen, Fed. Rep. of Germany

[21] Appl. No.: 932,934

[22] Filed: Nov. 20, 1986

[30] Foreign Application Priority Data

Apr. 14, 1986 [DE] Fed. Rep. of Germany ... 8610137[U]

[51] Int. Cl.⁴ ............................................. H01P 1/26
[52] U.S. Cl. .................................... 333/22 F; 333/248
[58] Field of Search .................................... 333/22 F

[56] References Cited

U.S. PATENT DOCUMENTS

| | | | |
|---|---|---|---|
| 2,560,536 | 7/1951 | Althouse | 333/22 F X |
| 2,752,572 | 6/1956 | Bird et al. | 333/22 F |
| 4,593,259 | 6/1986 | Fox et al. | 333/22 F |

Primary Examiner—Paul Gensler
Attorney, Agent, or Firm—Henry C. Nields

[57] ABSTRACT

A microwave calorimeter for very high power, with a housing, which surrounds a feed chamber, into which a waveguide runs for feeding the microwaves, and an absorber-chamber which is separated from the feed chamber by a dielectric wall and contains a microwave-absorbing fluid, the fluid consisting at least in part of a compound whose capacity for the absorption of microwaves is less than that of water.

13 Claims, 1 Drawing Sheet

MICROWAVE CALORIMETER

BACKGROUND OF THE INVENTION

1. Field of the Invention

The present invention relates to a microwave calorimeter for very high power, with a housing which surrounds a feed chamber into which a waveguide runs for feeding the microwaves, and an absorber-chamber which is separated from the feed chamber by a dielectric wall and contains a microwave-absorbing fluid.

2. Description of the Prior Art

There is known from U.S. Pat. No. 4,593,259 a microwave calorimeter for very high microwave power, which encloses an inner, cylindrical feed chamber (into one of the front sides of which a waveguide runs for the feeding of the microwaves) and an absorber-chamber surrounding the feed chamber like a jacket. The absorber-chamber is separated from the feed chamber by a dielectric wall, and it contains a microwave-absorbing fluid, namely, water. A coaxial cone-shaped reflector projects from the front wall of the feed chamber which lies opposite to the mouth of the waveguide, and this reflector reflects the microwaves which are fed axially through the waveguide outwardly to the absorber chamber.

Since the depth of penetration of the microwaves is continuously less with increasing frequency, such a "water load" has the disadvantage that the microwaves are finally absorbed only in a very thin water layer bordering on the dielectric wall, whereby at high power there can result bubble formation and boiling of the water in this thin layer. This leads in turn to a strong reflection of the power, whereby under certain circumstances the microwave generator (e.g. a gyrotron) and/or the absorber can be destroyed. It has been attempted to overcome this disadvantage by allowing the water to flow with high flow speed through the absorber chamber, in order to prevent the formation of vapor-bubbles or to remove along with the stream the bubbles which arise. However, this makes exact calorimetric measurements more difficult and in many cases it is not practical.

SUMMARY OF THE INVENTION

Accordingly, at the root of the present invention is the problem of improving a microwave calorimeter of the aforementioned type, so that a more uniform absorption in a greater volume of the absorber chamber can be obtained even at very high microwave frequencies, so that no disturbances can arise by way of bubble formation.

This problem is solved by the invention in the case of a microwave calorimeter for very high power, which contains a housing which surrounds a feed chamber (into which a waveguide runs for feeding of the microwaves) and an absorber-chamber (which is separated from the feed chamber by a dielectric wall and contains a microwave-absorbing fluid), by virtue of the fact that the fluid contains a chemical compound whose capacity for the absorption of microwaves is less than that of water; or, differently expressed, a compound with a greater absorption-length than water.

An especially suitable chemical compound is octanol ($C_8H_{18}O$), which has the additional advantage, to be neither inflammable nor poisonous, and not to boil until 195° C.

The absorption-length of the microwave frequency in question, or the wavelength, and the dimensions of the absorber-chamber can be optimally adapted by mixing octanol with weaker- or stronger-absorbing fluids, such as for example petroleum (very weak-absorbing) or methanol (very strong-absorbing).

Instead of octanol or in mixture therewith there can also be used other fluid alcohols, especially monovalent alcohols, especially with more than 6 C-atoms, such as heptanol or nonanol, as well as silicone oils.

Hereinafter there will be explained in more detail preferred embodiments of the invention, with reference to the drawings.

DESCRIPTION OF THE PREFERRED EMBODIMENTS

Figure 1:
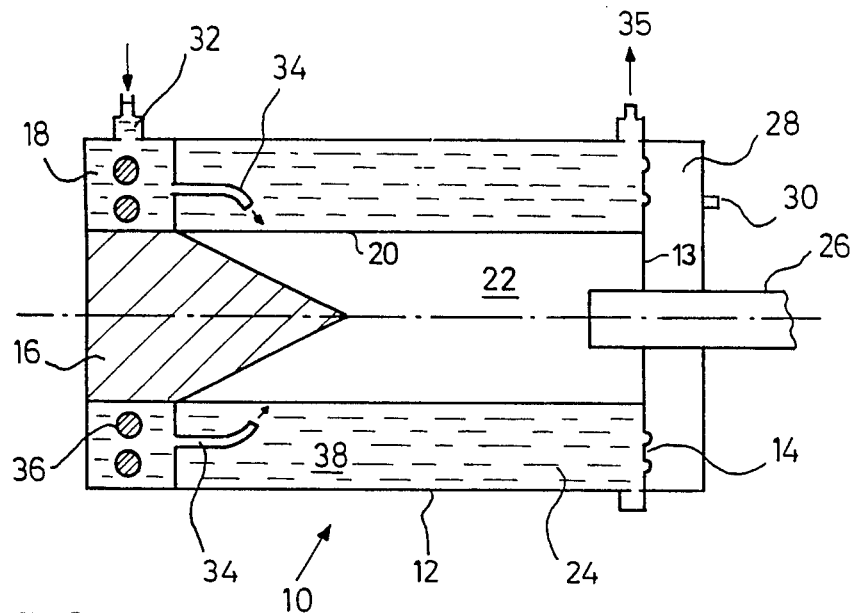
FIG. 1 shows a somewhat simplified axial section of a first embodiment of the microwave calorimeter according to the invention.

The microwave calorimeter which is shown in FIG. 1 has a housing (10) which is as radiation-proof as possible. The said housing has a cylindrical wall (12) of metal (e.g. stainless steel), a first metallic end wall (13), which contains a ring-shaped elastic membrane (14), and a second end wall, which is formed by a microwave-reflecting metal cone (16) as well as an inlet chamber (18) bordered by metallic walls. Spaced radially from the cylindrical wall (12) there is a separation-wall (20) of a dielectric material such as quartz glass, which separates an essentially cylindrical feed chamber (22) enclosing the axial region of the housing from an absorber chamber (24) which surrounds the feed chamber (22) coaxially like a jacket. A waveguide (26) runs into the feed chamber (22), which waveguide is brought through the end wall which is opposite to the metal cone (16). The metal cone (16), which serves as a microwave reflector, is preferable interchangeable, in order that the form of the reflecting surface can match the type of oscillation of the microwave radiation. At the side of the membrane (14) which is turned away from the absorber chamber (24) there is a pressure chamber (28), which is provided with a valve (30), so that the interior of the chamber (28) can be filled with a pressurized gas.

The inlet chamber (18) is provided with an inlet connection (32) for coolant fluid and is connected with the interior of the absorber-chamber (24) through a number (e.g. twelve) of nozzles (34) which project into the interior of the absorber-chamber (24) with their openings facing the separation-wall (20). The openings of the nozzles (34) can exhibit a certain inclination in the circumferential direction, so that a spiral stream results along the dielectric separation-wall (20). The absorber-chamber (24) is in turn provided with an exit connection (35), which is arranged at the side of the cylincrical wall (12) which is opposite to the inlet connection (32).

In the inlet chamber (18) there is located a resistance-heating element (36), with which the microwave calorimeter can be calibrated.

According to a preferred embodiment of the invention, the absorber-chamber (24) contains a fluid (38), which consists entirely or partly of octanol ($C_8H_{18}O$). The fluid can also be a mixture of octanol with another mixture, which is stronger or weaker in absorbing the microwaves to be absorbed. In this way the absorption length of the microwaves, which are fed through the waveguide (26) and are reflected by the metal cone (16) through the dielectric separation wall (20) into the fluid (38), may be matched to the radial dimensions of the fluid-filled absorber-chamber (24), so that the absorption of the microwaves is distributed over the entire volume of the absorbing fluid in the absorber-chamber, and a surface heating as well as bubble formation are avoided.

In the case of the absorption of microwave impulses of high power, pressure shocks can arise in the absorber-space (24), which in the above-described microwave calorimeter can be taken up by the suitably formed (e.g. wavy) annular metal membrane (14). The metal membrane (14) can be biased by a pressurized gas in the chamber (28), which is especially advantageous when the fluid (38) is under a certain excess pressure.

The microwave calorimeter according to FIG. 1 lends itself not only to power measurement with axially symmetric modes (TEon - modes) but also with lineally polarized wave-types (TE11 - or HE11 - modes) or a mixture of both.

Figure 2:
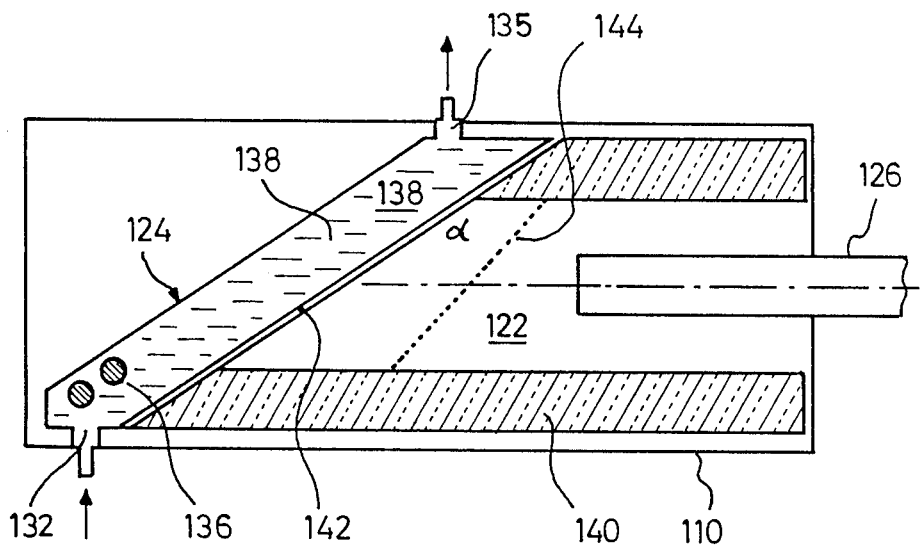
FIG. 2 shows a somewhat simplified axial section of a second embodiment of the microwave calorimeter according to the invention, which is adapted especially to exact determination of a lineally polarized part contained in the microwave radiation.

The embodiment of the microwave calorimeter according to the invention shown in FIG. 2 is used for exact determination of a lineally polarized part of the microwave radiation. The microwave calorimeter according to FIG. 2 contains a cylindrical housing (110) of stainless steel, which contains a feed-chamber (122), into which runs a waveguide (126) which is led in through one of the end walls of the housing. The feed chamber (122) is surrounded by a solid absorber (140) arranged in the housing (110), which preferably consists of microwave-absorbing ceramic, such as fire-clay, and has the form of a hollow cylinder, the end whereof which is turned away from the waveguide (126) is cut off diagonally at an angle alpha and is closed by a thin, planar dielectric window (142). Behind the window (142) there is a flat absorber-chamber (124), which exhibits an inlet connection (132) as well as an outlet connection (135) for a fluid (138) of the type explained in connection with FIG. 1 which absorbs the microwaves. The angle of incidence alpha of the dielectric window, which e.g. can consist of quartz glass or Al2O3 or PTFE, corresponds to the Brewster angle for the lineally polarized part of the oscillation.

In the cylindrical feed chamber (122) an interchangeable polarization filter (144) is arranged between the mouth of the waveguide (126) and the dielectric window (142). This filter transmits only the lineally polarized radiation to be measured, and reflects the other parts into the solid absorber (140) which preferably consists of fire-clay, where they are absorbed, so that they do not participate in the calorimetric measurement by means of the fluid in the absorber-chamber (124). The polarizing filter 144 can be a known device essentially consisting of spaced parallel elongated metal members, as wires supported by a suitable frame which is mounted interchangeably in the absorber chamber.

In the absorber-chamber (124) there is arranged an electric heater-spiral (136) for calibration of the calorimeter.

The feed chamber (122) can be provided with an apparatus for removing the heat which arises in the solid absorber (140), e.g. with connections for the passage therethrough of cooling air.

Instead of octanol, or in mixture with it, a silicone oil can also be used for absorption, which silicone oil has a suitable absorption-capacity for the microwaves to be absorbed.

Having thus described the principles of the invention, together with illustrative embodiments thereof, it is to be understood that, although specific terms are employed, they are used in a generic and descriptive sense, and not for purposes of limitation, the scope of the invention being set forth in the following claims.

We claim:

1. Microwave calorimeter for very high power, comprising, in combination, a housing, a feed chamber mounted within said housing and surrounded thereby, a waveguide mounted so as to run into said feed chamber so as to feed microwaves thereinto, and an absorber-chamber, and a dielectric wall which separates said absorber-chamber from said feed chamber, said absorber-chamber containing a microwave-absorbing fluid which consists at least in part of a fluid alcohol with at least six carbon atoms.

2. Microwave calorimeter according to claim 1, wherein said fluid comprises octanol.

3. Microwave calorimeter for very high power, comprising, in combination, a housing, a feed-chamber mounted within said housing and surrounded thereby, a waveguide mounted so as to run into said feed chamber so as to feed microwaves thereinto, a disk-shaped absorber-chamber arranged with its plane diagonal to the axis of said waveguide, a hollow cylinder-shaped solid absorber surrounding said feed chamber and comprising a microwave-absorbing ceramic and having an extremity turned away from said waveguide which is diagonal, and a dielectric wall which separates said absorber-chamber from said feed chamber, said absorber-chamber containing a microwave-absorbing fluid.

4. Microwave calorimeter according to claim 3 having a thin, disk-shaped dielectric window arranged between said feed chamber and said absorber-chamber.

5. Microwave calorimeter according to claim 3 wherein the side of said absorber-chamber which is turned towards said waveguide extends in the Brewster angle to the axis of said waveguide.

6. Microwave calorimeter according to claim 3 wherein the side of the dielectric window which is turned towards said waveguide extends in the Brewster angle to the axis of said waveguide.

7. Microwave calorimeter according to claim 3 wherein the sides of said absorber-chamber and the dielectric window which are turned towards said waveguide extend in the Brewster angle to the axis of said waveguide.

8. Microwave calorimeter according to claim 3 having a polarization filter arranged in said feed chamber between said waveguide and said absorber-chamber, which filter reflects undesired wave components and transmits essentially only the desired wave components to said absorber-chamber.

9. Microwave calorimeter according to claim 8, wherein said polarization filter is mounted interchangeably.

10. Microwave calorimeter for very high power, comprising, in combination, a housing, a feed chamber mounted within said housing and surrounded thereby, a waveguide mounted so as to run into said feed chamber so as to feed microwaves thereinto, and an absorber-chamber, and a dielectric wall which separates said absorber-chamber from said feed chamber, said absorber-chamber containing a microwave-absorbing fluid, wherein a part of the wall of said absorber-chamber consists of an elastic metal membrane.

11. Microwave calorimeter according to claim 10, wherein a pressure medium chamber is arranged at that side of said membrane which is turned away from said absorber-chamber.

12. Microwave calorimeter for very high power, comprising, in combination, a housing, a feed chamber mounted within said housing and surrounded thereby, a waveguide mounted so as to run into said feed chamber so as to feed microwaves thereinto, and an absorber-chamber, and a dielectric wall which separates said absorber-chamber from said feed chamber, said absorber-chamber containing a microwave-absorbing fluid, wherein said absorber-chamber surrounds said feed-chamber like a jacket, said calorimeter having an inlet chamber arranged at a front side of said absorber-chamber, a fluid-inlet connetion mounted on said inlet chamber, and at least one nozzle arranged for providing communication between said inlet chamber and the interior of said absorber-chamber.

13. Microwave calorimeter according to claim 12, wherein said inlet chamber is annular and has a central aperture, and wherein a microwave reflector element is removably mounted in said central aperture.

* * * * *